US008177751B2

(12) United States Patent
Feldmann et al.

(10) Patent No.: US 8,177,751 B2
(45) Date of Patent: May 15, 2012

(54) CONVEYING DEVICE IN OR FOR AN APPARATUS FOR ADMINISTERING A DRUG

(75) Inventors: Peter Feldmann, Oberburg (CH); Roger Haenggi, Nunningen (CH); Hanspeter Niklaus, Riken (CH)

(73) Assignee: Roche Diagnostics International AG, Steinhausen (CH)

( * ) Notice: Subject to any disclaimer, the term of this patent is extended or adjusted under 35 U.S.C. 154(b) by 105 days.

(21) Appl. No.: 12/685,262

(22) Filed: Jan. 11, 2010

(65) Prior Publication Data

US 2010/0179476 A1 Jul. 15, 2010

Related U.S. Application Data

(63) Continuation of application No. PCT/EP2008/058936, filed on Jul. 9, 2008.

(30) Foreign Application Priority Data

Jul. 12, 2007 (EP) .................................... 07112391

(51) Int. Cl.
*A61M 37/00* (2006.01)

(52) U.S. Cl. ........................................................ 604/155

(58) Field of Classification Search ................... 604/131, 604/154, 155, 207, 208, 211, 220, 221, 224
See application file for complete search history.

(56) References Cited

U.S. PATENT DOCUMENTS

| | | | |
|---|---|---|---|
| 1,751,139 A | 3/1930 | Feinstein | |
| 1,905,569 A | 4/1933 | Rapellin | |
| 2,627,270 A * | 2/1953 | Glass | 604/155 |
| 2,900,148 A * | 8/1959 | Nickels | 244/224 |
| 4,769,009 A * | 9/1988 | Dykstra | 604/155 |
| 5,017,190 A * | 5/1991 | Simon et al. | 604/207 |
| 5,083,477 A * | 1/1992 | Geil | 74/553 |
| 5,300,041 A * | 4/1994 | Haber et al. | 604/207 |
| 6,117,142 A | 9/2000 | Goodson et al. | |
| 6,800,071 B1 * | 10/2004 | McConnell et al. | 604/155 |
| 6,817,990 B2 * | 11/2004 | Yap et al. | 604/228 |
| 6,854,620 B2 * | 2/2005 | Ramey | 222/63 |
| 6,972,007 B2 * | 12/2005 | Geiser et al. | 604/211 |
| 7,273,472 B2 * | 9/2007 | Peter et al. | 604/155 |
| 7,862,544 B2 * | 1/2011 | Peter et al. | 604/155 |
| 2003/0060767 A1 * | 3/2003 | Peter et al. | 604/151 |
| 2006/0079831 A1 * | 4/2006 | Gilbert | 604/31 |
| 2006/0190001 A1 * | 8/2006 | Powell | 606/96 |

FOREIGN PATENT DOCUMENTS

WO 2005/094921 A 10/2005

* cited by examiner

*Primary Examiner* — Jackie Ho
*Assistant Examiner* — Diva K Chander
(74) *Attorney, Agent, or Firm* — Dinsmore & Shohl LLP (57) ABSTRACT

A conveying device in or for an apparatus for administering a product, including a base, a first conveying member which can be moved relative to the base and includes a first thread, a second conveying member which can be moved relative to the base and includes a second thread for a threaded engagement with the first thread, wherein the second thread extends over an axial portion of the second conveying member which is radially flexible in relation to its threaded axis, such that one of the conveying members can be axially inserted into the other in an overlap of the threads, and a blocking member which can be moved relative to the base, wherein one of the blocking member and the second conveying member can be moved relative to the other into a blocking position in which the blocking member radially stiffens the second thread in the threaded engagement in the region of the flexible axial portion and thus secures the threaded engagement.

23 Claims, 3 Drawing Sheets

CONVEYING DEVICE IN OR FOR AN APPARATUS FOR ADMINISTERING A DRUG

CROSS-REFERENCE TO RELATED APPLICATION

This application is a continuation of International Patent Application No. PCT/EP2008/058936, filed on Jul. 9, 2008 which claims priority to European Application No. 07112391.3, filed on Jul. 12, 2007, the entire contents of both of which are incorporated herein by reference.

BACKGROUND

The present invention relates to devices for injecting, infusing, administering, delivering or dispensing a substance, and to methods of making and using such devices. More particularly, it relates to a conveying device in or for an apparatus for administering a product. In some embodiments, the apparatus can be an infusion apparatus or injection apparatus for administering a drug, a diagnostic agent or in principle any other product which can be administered to a human or animal subject. One preferred application or use of the device and method of the present invention is for the self-administering of drugs, in particular administering insulin in the treatment of diabetes.

In many cases, infusion apparatus and injection apparatus for administering the product in exact doses employ a threaded drive to convert a torque of a drive motor into an axial translational movement of a conveying member in the threaded engagement and to deliver the product from a reservoir of the infusion apparatus or injection apparatus by the axial movement. Once the reservoir has been emptied, the conveying member has to be rotated back in the threaded engagement into an initial position to be used again, which can either be laboriously performed manually or requires a direction-reversible drive motor which consumes energy for the reverse rotation.

WO 2005/094921 A1 proposes a threaded drive comprising two conveying members in a threaded engagement, one of which is slit in the region of its thread and is therefore radially flexible. The relevant conveying member can therefore be axially pushed into threaded engagement with the other conveying member, up to and against a stopper, without a rotational movement. to be able to establish the threaded engagement in the stopper position despite the radial flexibility, however, the conveying member which is flexible in the region of its thread has to be rotated about the threaded axis in the stopper position. Establishing the threaded engagement requires a particular hand operation and therefore particular concentration and dexterity at the end of axial insertion. This is in particular problematic for applications in which the user administers the product himself, for example in the treatment of diabetes. WO 2005/094921 A1 also describes a modified mechanism in which the threaded engagement is automatically established when the conveying member is pushed in. In the modification, a flexible thread region is created by segments which project radially with respect to the threaded axis, can be elastically bent and are therefore correspondingly slender, and which together form the thread of the conveying member. When the conveying member is pushed in, the bendable segments slide elastically over the thread of the other conveying member. In the threaded engagement, the segments forming the flexible thread therefore always press, with their spring force which is based on bending elasticity, into the turns of the thread of the other conveying member. A corresponding amount of energy is needed for the drive.

SUMMARY

It is an object of the present invention to provide a conveying device comprising conveying members which can easily be moved into a free-moving threaded engagement with each other by an axial movement to be performed relative to each other.

In one embodiment, the present invention comprises a conveying device in or for an apparatus for administering a product, comprising a base, a first conveying member which can be moved relative to the base and comprises a first thread, a second conveying member which can be moved relative to the base and comprises a second thread for a threaded engagement with the first thread, wherein the second thread extends over an axial portion of the second conveying member which is radially flexible in relation to its threaded axis, such that one of the conveying members can be axially inserted into the other in an overlap of the threads, and a blocking member which can be moved relative to the base, wherein one of the blocking member and the second conveying member can be moved relative to the other into a blocking position in which the blocking member radially stiffens the second thread in the threaded engagement in the region of the flexible axial portion and thus secures the threaded engagement.

In one embodiment, the present invention comprises a conveying device in or for an apparatus for administering a product which can be administered to a human or animal subject, which comprises a base, a first conveying member which can be moved relative to the base, and a second conveying member which can be moved relative to the base. The first conveying member is provided with a first thread and the second conveying member is provided with a second thread. The threads are in a threaded engagement with each other when the product is being administered, such that the conveying members together form a threaded drive. The second thread extends over an axial portion of the second conveying member which is radially flexible in relation to its threaded axis, such that one of the conveying members can be axially pushed into the other in an overlap of the threads, and a relative rotational movement between the conveying members is not required to establish the axial overlap. The base forms a frame for the first and second conveying member. In some embodiments, the base can comprise a casing of the administering apparatus, in which other components of the administering apparatus—for example, a reservoir for the product—are accommodated. The base can also, however, be an attached part or, in some preferred embodiments, an installed part which is arranged on or in such a casing of the administering apparatus or is provided for such an arrangement.

In accordance with the present invention, in some embodiments, the conveying device comprises, in addition to the components cited, a blocking member which can be moved relative to the second conveying member or relative to which the second conveying member can be moved into a blocking position in which the blocking member holds the second thread in the threaded engagement with the thread of the first conveying member by radially stiffening the flexible axial portion. In the blocking position, the blocking member prevents the second thread from being able to be moved out of the threaded engagement by an axial load, due to the flexibility of the axial portion. Because the flexible axial portion and therefore the second thread is stiffened by a blocking member which is additionally provided, it is possible to establish the threaded engagement of the conveying members without relative rotation. It is also not necessary to form any filigree bending tongues which necessarily clamp in the threaded engagement, since a restoring elasticity force of the conveying member does not have to ensure the threaded engagement, but rather the additional blocking member serves to stiffen the radially flexible thread. Depending on the geometry of the second conveying member in the region of the second thread, the blocking member in the blocking position can also press the second thread into the threaded engagement with a small radial pressing force, wherein, in some preferred embodiments, the pressing force exists only between the blocking member and the second conveying member and not between the two threads. The blocking member and the second conveying member can have a point contact, line contact or area contact, wherein the points, lines or areas which contact each other are offset with respect to each other in the circumferential direction about the threaded axis at least substantially by 180°.

For establishing the threaded engagement, the blocking member is moved into the blocking position not only relative to the second conveying member but also simultaneously relative to the base and the first conveying member. For an alternative embodiment, however, it is also conceivable for the blocking member to assume the blocking position before the threaded engagement is established, and to enter an engagement with the second conveying member in the final moment of the relative insertion movement between the conveying members, in which it stiffens its flexible axial portion at least in the region of the second thread, to secure the second thread against flexing under a load in the threaded engagement with the first thread. In such an alternative embodiment, the engagement is also configured such that during its conveying movement, the second conveying member slaves the blocking member relative to the first conveying member. To this end, the blocking member and the second conveying member can, for example, hook together. The second conveying member collects the blocking member from the blocking position, so to speak, so that the blocking member provides for the stiffening in the region of the thread during administering. As a result, the blocking member can thus be moved at least relative to the second conveying member into the blocking position, which also includes the case in which it is not the blocking member but rather the second conveying member which is moved relative to the first conveying member and, in some preferred embodiments, also relative to the base, until the engagement with the blocking member which stiffens the thread is established. For stiffening the second thread, at least the blocking member and the second conveying member are moved relative to each other into the blocking position. In one preferred variant, the blocking member is moved relative to the second conveying member and also relative to the first conveying member and the base for this purpose. In a second variant, the blocking member is moved relative to the first conveying member and the base, at least while the product is being administered. The blocking member can thus be moved relative to the first conveying member and the base. To be able to fulfil the stiffening function, the blocking member is formed so as to conform to the flexible axial portion of the second conveying member or at least to said axial portion in the region of the thread.

In some preferred embodiments, the blocking member can be moved relative to the second conveying member, or the second conveying member can be moved relative to the blocking member, in the axial direction, i.e. along the threaded axis, e.g. centrically with respect to the second thread on the threaded axis, into the blocking position. The blocking member performs the movement into the blocking position both relative to the second conveying member and relative to the first conveying member and, in some preferred embodiments, also relative to the base. The blocking member and the second conveying member are moved in the same axial direction relative to the first conveying member, the second conveying member into the axial overlap of the threads, and the blocking member into the blocking position.

In some preferred embodiments, in its conveying movement as performed relative to the first conveying member in the course of administering the product, the second conveying member slaves the blocking member, such that the blocking member always provides for the stiffening in the region of the second thread. The second conveying member mounts or carries the blocking member directly.

In some preferred embodiments, the blocking member in the blocking position is axially fixed relative to the second conveying member. The fixation can in principle be a non-positive fit, including a purely non-positive fit, but in some preferred embodiments, is a positive fit or at least comprises a positive-fit engagement. In some preferred embodiments, the fixation can be formed by a locking engagement which exists directly between the blocking member and the second conveying member.

In one embodiment, the blocking member can be moved out of a releasable fixing engagement—which can be formed as a purely non-positive fit or a purely positive fit or a positive and non-positive fit, e.g. a suitable locking engagement—relative to the second conveying member, out of an initial position into the blocking position. The fixing engagement which holds the blocking member in the initial position can exist directly between the blocking member and the second conveying member.

The second conveying member and the blocking member can form a piston rod together, if the administering apparatus conveys the product by a piston which can be axially moved in the reservoir. In such embodiments, the blocking member may form a front end of the piston rod which is connected to the piston, abuts or faces the piston.

In some preferred embodiments, the blocking member and the second conveying member together form a telescope. The telescope is retracted, i.e. its axial length is reduced, for stiffening the second thread. The blocking member protrudes into the second conveying member; however, these conditions can in principle be reversed, depending on whether the second thread is embodied as an inner thread or as an outer thread.

In some preferred embodiments, the axial flexibility of the axial portion provided with the second thread can be obtained in the relevant axial portion by one or more axially extending breach(es), opening(s) or relieved regions(s) in the second conveying member. The breaches advantageously extend up to an axial end of the second conveying member, such that the flexible axial portion of the second conveying member comprises a number of axially extending arms which converge, away from the relevant axial end, in a conjoining portion of the second conveying member. At least one of the arms, in some preferred embodiments a number of the arms and/or all of the arms, adopts the thread function together, by each arm forming an arc segment of the thread on a circumferential surface. It would in principle also be sufficient for the second conveying member to comprise only one arm which is radially flexible and forms a threaded segment. In some preferred embodiments, the second conveying member comprises a number of arms, for example four arms, which are for example obtained by a cross-shaped slit in the second conveying member, in a view onto the rear end of said conveying member. In some preferred embodiments, the flexible axial portion of the second conveying member comprises two arms which are obtained by a single, axially extending slit. The arms are axially extending bending arms, i.e. they can be bent radially inwardly or outwardly from the respective axial fastening end, into the threaded engagement, such that the circumferential surface of the respective arm which is provided with the respective threaded segment points transverse to the direction in which said threaded segment is moved into the threaded engagement.

Although in some embodiments it would be sufficient for the second thread to only comprise a single turn or to even only extend over an angle of less than 360° about the threaded axis, in some preferred embodiments the second thread comprises more than one complete turn, e.g. a number of complete turns of the thread. On the other hand, it comprises significantly fewer turns of the thread than the first thread, i.e. in preferred embodiments, it is significantly shorter axially than the first thread. The first thread thus comprises several times more turns than the second thread.

In some preferred embodiments, the second thread, more specifically its circumferential covering surface, is cylindrical in its stiffened state, when the flexible axial portion of the second conveying member abuts the blocking member in the region of the second thread. This also contributes to a free-moving, smooth threaded engagement. In a preferred variant, this also corresponds to the unloaded state of the flexible axial portion. In other variants, however, the flexible axial portion can also, for example, be inclined linearly or in a curve with respect to the threaded axis. In these other variants, the circumferential covering surface of the second thread is cylindrical when the blocking member is in the blocking position, i.e. it is moved into the cylindrical shape by the blocking member.

In some preferred embodiments, the second conveying member and the blocking member are designed to be used once only, and are exchanged for a new second conveying member and a new blocking member when the reservoir is exchanged or refilled. By contrast, the first conveying member and the base are preferably used repeatedly. In such a design, it may be advantageous for the second conveying member to be formed from a softer material than the first conveying member, or at least for the second thread to be formed using a softer material than the first thread. In some preferred embodiments, the conveying members and the blocking member are each formed in one piece, for example formed from plastic by injection molding. One of the conveying members or both conveying members or the blocking member can in principle also consist of a number of separately formed parts which are respectively connected to each other such that they respectively perform the movements required for establishing the threaded engagement and when conveying the product as a unit.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figures 1, 2:
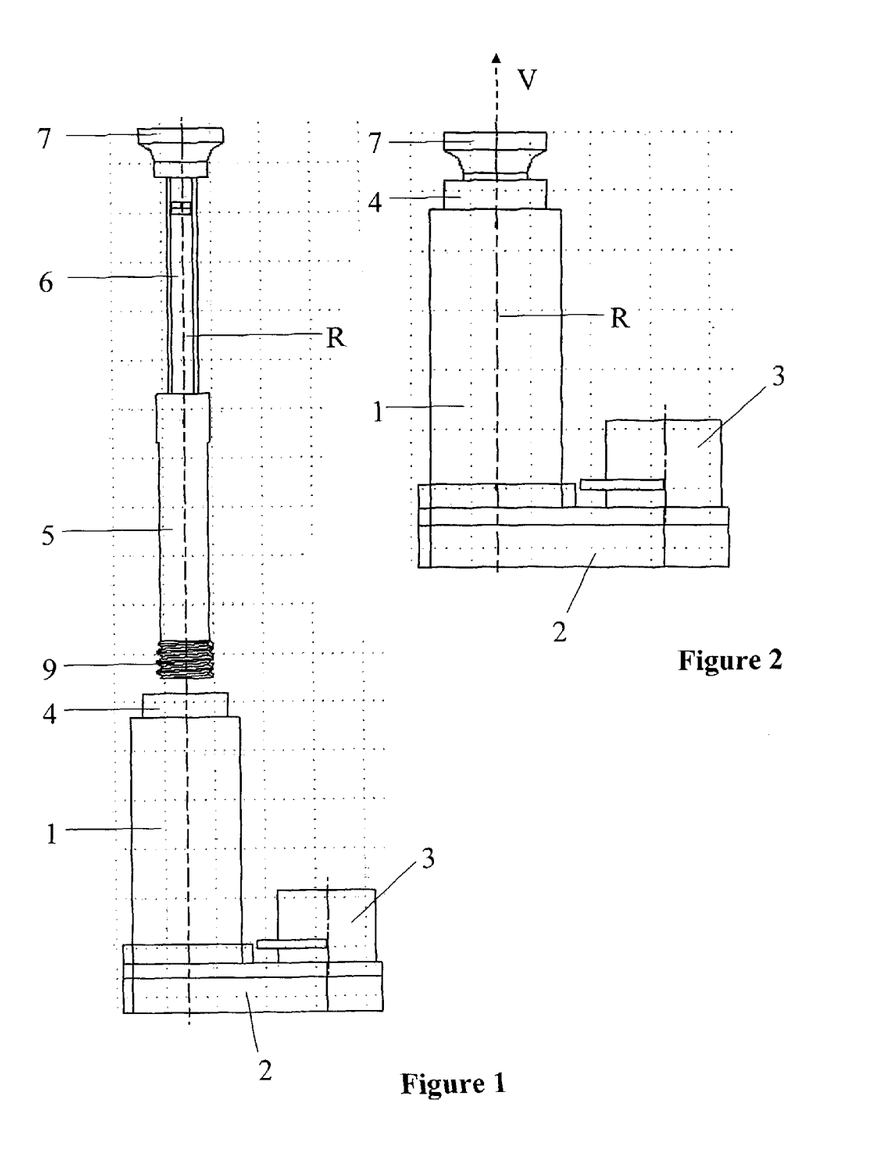
FIG. 1 depicts one embodiment of a conveying device in accordance with the present invention in an initial state, before a threaded drive comprising two conveying members is assembled.
FIG. 2 depicts the conveying device of FIG. 1, after assembly.

FIG. 1 shows a conveying device of an apparatus for administering a fluid product. In this exemplary embodiment, the apparatus is formed by an infusion pump for subcutaneously administering a fluid drug, for example insulin, which can be worn on the body, on or underneath one's clothing. The conveying device shown in FIG. 1 can be arranged in a casing of such an apparatus. It serves to convey the product contained in a reservoir. A piston is movably arranged in the reservoir. to be administered, the product is conveyed by advancing the piston in an axial direction toward an outlet of the reservoir. The conveying device serves to advance such a piston.

The conveying device comprises bearing structures 1 and 2 which together form a base for mounting and supporting other components of the conveying device. The conveying device also comprises a motorized drive 3, a first conveying member 4, a second conveying member 5 and a blocking member 6. The first conveying member 4 can be rotated about a rotational axis R relative to the base and is axially fixed. The axial fixation relative to the base can be absolute, within production tolerances. In one variant, smaller axial stroke movements along the rotational axis R can also be possible, for example to measure an axial force which acts on the conveying member 4 when the product is being conveyed. The second conveying member 5 is shown in FIG. 1 detached from the first conveying member 4, before the conveying device is assembled.

FIG. 2 shows the conveying device in its assembled state. The second conveying member 5 protrudes or extends into the first conveying member 4. In the assembled state, the conveying members 4 and 5 are in threaded engagement with each other, the threaded axis of which is the rotational axis R which is therefore referred to in the following as the threaded axis R. The drive 3 is coupled to the first conveying member 4 in the region of the bearing structure 2 by a gear. The gear can, for example, be a toothed wheel gear. The drive 3 is a rotary motor, for example an electric step motor, having a motor axis which is parallel to the threaded axis R. The gear can, for example, accordingly be a simple spur wheel gear. The first conveying member 4 is connected non-rotationally to a gear wheel, which also includes the case in which such a gear wheel can be formed in one piece with the conveying member 4.

The second conveying member 5 and the blocking member 6 together form a piston rod which is axially moved relative to the base and the conveying member 4 when the conveying member 4 is rotary-driven while the conveying members 4 and 5 are in threaded engagement. In an axial movement in an advancing direction V, the piston rod presses against the piston, such that the piston is likewise moved in the advancing direction V toward the outlet of the reservoir and product is delivered in accordance with the advancing movement. At its front end in the advancing direction V, the blocking member 6 comprises a plunger 7 with which it presses against the piston in the advancing direction V and thus advances the piston. There is pressing contact between the piston rod and the piston only in the advancing direction V. There is no connection in the opposite direction, such that the piston rod can easily be detached from the piston by a movement relative to the piston and counter to the advancing direction V.

Figure 3:
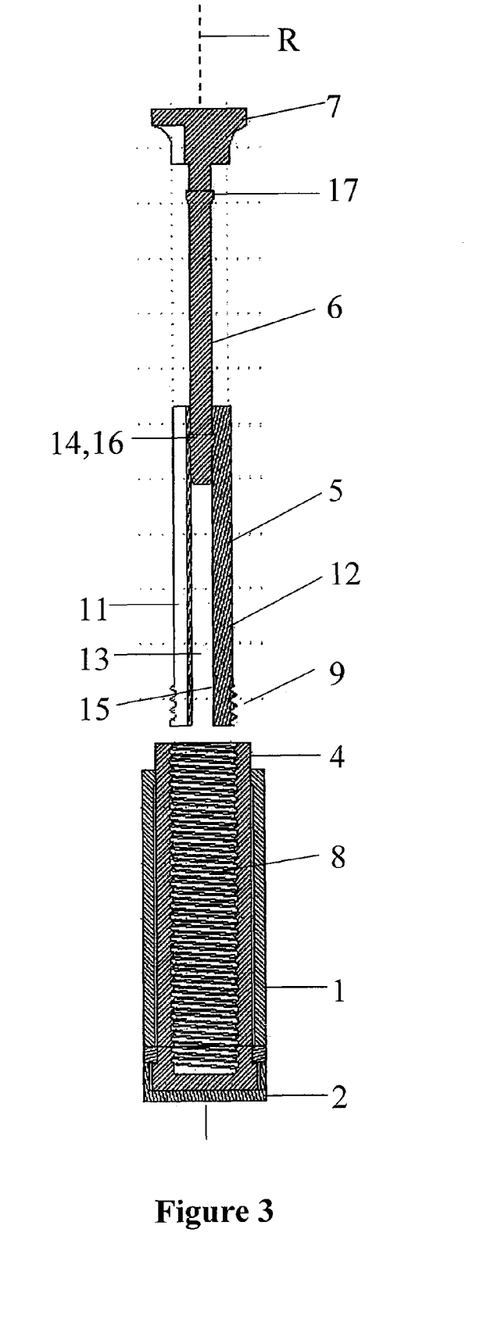
FIG. 3 depicts the conveying device of FIG. 1 in its initial state, in a longitudinal section.
Figure 4:
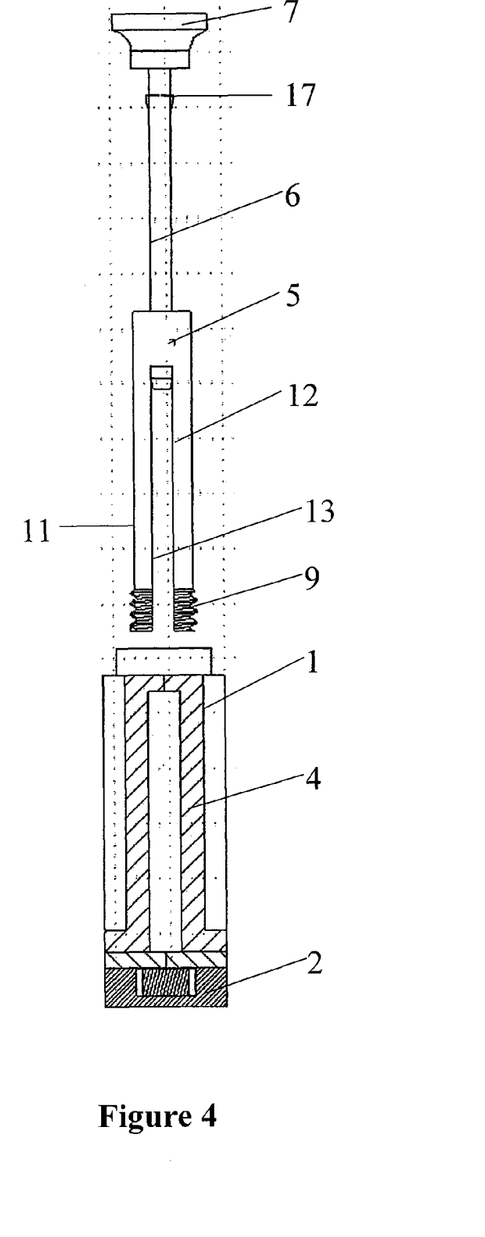
FIG. 4 depicts the conveying device of FIG. 1 in its initial state, in a partial view and a partial longitudinal section.

FIG. 3 shows a longitudinal section of the conveying device, in a sectional plane which is at right angles to the plane of view in FIG. 1. The threaded axis R extends in the sectional plane. FIG. 4 shows the conveying device in a sectional plane of view which is offset in parallel with respect to the sectional plane in FIG. 3 and extends through the conveying member 4 at a distance from the piston rod. In FIGS. 3 and 4, as in FIG. 1, the conveying device is not yet in its assembled state.

Starting from the initial state shown in FIG. 3, the piston rod—i.e. the combination of the conveying member 5 and the blocking member 6—can be axially inserted into the conveying member 4, counter to the advancing direction V, up to an axial stopper position. The stopper position shown in FIG. 2 is determined by a stopper contact between the conveying member 5 and a stopper which in this exemplary embodiment is formed by the conveying member 4, but which in modifications could also for example be formed by the base, for example by the bearing structure 2.

The conveying member 4 is a sleeve structure comprising a sleeve portion and a bottom at an axially rear end. The sleeve portion extends over almost the entire axial length of the conveying member 4. A first thread 8 is formed on an inner surface area of the sleeve portion. The thread 8 extends over the entire length of the sleeve portion of the conveying member 4. The conveying member 4 could also be formed without the bottom, as an axially continuous sleeve. In such modifications, the thread 8 could axially extend continuously over the entire length of the conveying member 4.

At its rear end, the conveying member 5 comprises a second thread 9 on its outer circumference, which is formed, as an outer thread, so as to conform to the first thread 8, for the threaded engagement with the first thread 8. The thread 9 only extends over a smaller part of the axial length of the thread 8, but nonetheless comprises a number of turns of the thread, to ensure a non-clamping and therefore free-moving but still fixed threaded engagement. The conveying member 5 is substantially likewise sleeve-shaped and, in a front region, comprises a sleeve portion which is self-containing in the circumferential direction about the threaded axis R, and arms 11 and 12 which axially project backwards from the sleeve portion, counter to the advancing direction V, and on which the thread 9 is formed. The arms 11 and 12 each form an arc segment of the thread 9 on their outer circumference. Each of the arc segments extends over an angle of less than 180° in the circumferential direction about the threaded axis R. The thread 9 extends up to the axial rear end on each of the arms 11 and 12. The arms 11 and 12 are separated from each other on both their sides, each by a breach or opening 13 which extends at the front end of the conveying member 5 continuously from the sleeve portion to the rear end of the conveying member 5. The arms 11 and 12 can be elastically bent toward each other, into the breaches 13, as long as the space between the arms 11 and 12 is free. In its shape, the conveying member 5 corresponds to a cylindrical sleeve which is continuously slit from its rear end to the front sleeve portion, such that the breaches 13 each have the shape of linear axial slits. The arms 11 and 12 form a flexible axial portion of the conveying member 5 and a radially flexible thread 9.

In the initial state of the conveying device shown in FIGS. 1, 3 and 4, the blocking member 6 assumes an axial initial position relative to the conveying member 5. In the initial position, only its axially rear end portion protrudes into the front sleeve portion of the conveying member 5. In the initial position, the blocking member 6 is releasably fixed in the axial direction relative to the conveying member 5. In this exemplary embodiment, the fixing engagement is formed directly between the conveying member 5 and the blocking member 6, as a locking engagement. A first lock element or locking means 14 of the conveying member 5 and a first locking counter element of locking counter means 16 of the blocking member 6 are locked to each other in the locking engagement. The blocking member 6 can only be moved out of this fixing engagement against a restoring elasticity force, counter to the advancing direction V; a relative movement in the advancing direction V is prevented by the fixing engagement. The locking means 14 is formed on an inner surface area of the conveying member 5, in the form of recesses. Two such locking means 14 are formed in this exemplary embodiment, offset with respect to each other by 180° in the circumferential direction. The locking counter means 16 is correspondingly formed on the outer circumference of the blocking member 6 as radially projecting locking cams. In this exemplary embodiment, locking counter means 16 which are arranged on the blocking member 6 are formed in accordance with the number of locking means 14 and so as to conform. Instead of forming each of the locking means 14 as a recess and each of the locking counter means 16 as a bump or cam, the locking means 14 could also be formed as bumps or cams and the locking counter means 16 as recesses; hybrid forms are equally conceivable. The locking means 14 and locking counter means 16 could also each consist of only a single locking means 14 and correspondingly a single locking counter means 16; however, in some preferred embodiments, there is a uniform distribution of a number of locking means 14 and locking counter means 16 in the circumferential direction about the threaded axis R.

In the initial position, the blocking member 6 axially protrudes only far enough into the conveying member 5 that it does not obstruct the bending movement of the arms 11 and 12 toward each other, or at least does not prevent the movement of the arc segments of the thread 9 toward each other. The blocking member 6 can be axially moved relative to the conveying member 5, counter to the advancing direction V, from the initial position into a blocking position in which it protrudes into the space between the arc segments of the thread 9 which in the initial position was still free, and radially fills the space between the arc segments of the thread 9. When the blocking member 6 assumes the blocking position relative to the conveying member 5, the arc segments of the thread 9 can therefore no longer be moved toward each other, transverse to an imaginary circumferential covering surface of the thread 9, such that the axial portion which is still flexible in the initial position of the blocking member 6 and comprises the thread 9 is stiffened, and forms a rigid threaded portion with the blocking member 6 which is in the blocking position.

In the blocking position, the blocking member 6 is axially fixed relative to the conveying member 5. This other fixing engagement is also formed directly between the conveying member 5 and the blocking member 6. It is automatically set when the blocking member 6 is pressed out of the initial position into the blocking position, deeper into the conveying member 5. This second fixing engagement is likewise formed as a locking engagement, namely between a second lock element or locking means 15 of the conveying member 5 and the first locking counter means 16 of the blocking member 6. In accordance with whether the locking counter means 16 is formed as one or more cams, the second locking means 15 is also formed as one or more recess(es)—in this exemplary embodiment, with one recess on an inner surface area of each of the arms 11 and 12, respectively. To strengthen the fixing engagement in the blocking position of the blocking member 6, the blocking member 6 is also provided with a second locking counter means 17 which, in the blocking position, enters a fixing engagement—in in this exemplary embodiment, a locking engagement—with the first locking means 14 of the conveying member 5. That which has been said with respect to the locking means 14 and the locking counter means 16 for the fixing engagement in the initial position also applies equally to the second locking means 15 and the second locking counter means 17 and the respective fixing engagement in the blocking position of the blocking member 6.

Figure 5:
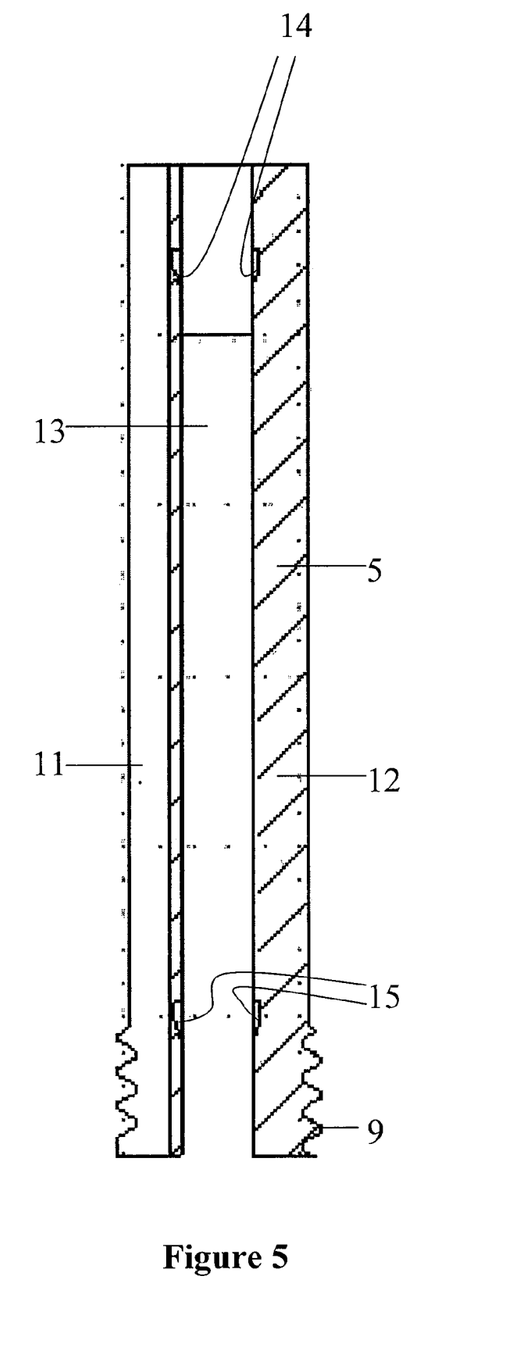
FIG. 5 depicts an embodiment of one of the conveying members of FIG. 1 in a longitudinal section.
Figure 6:
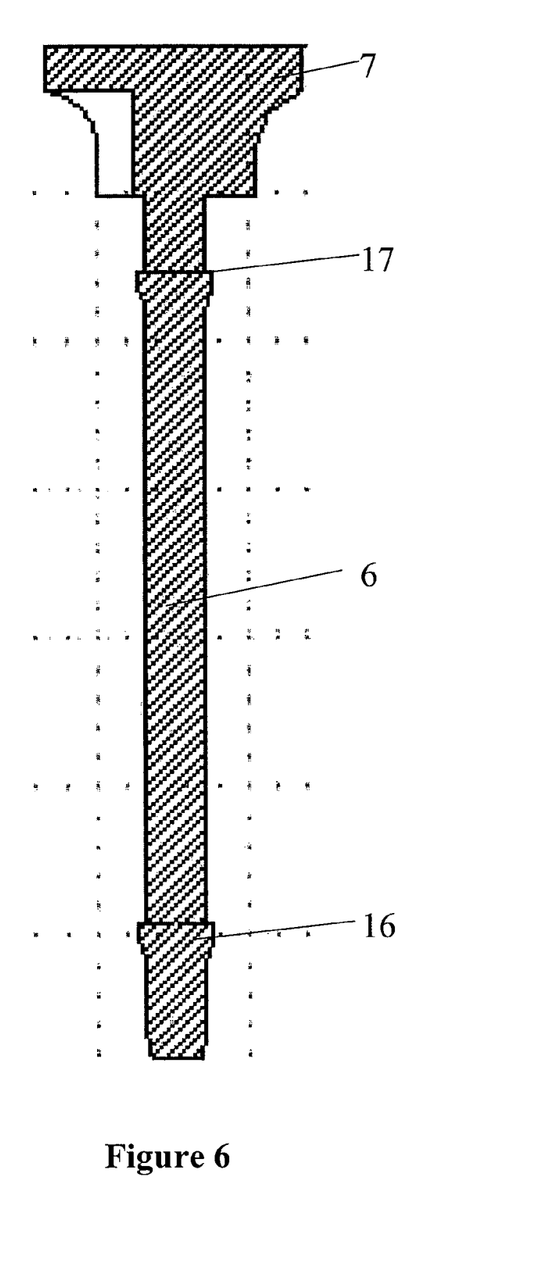
FIG. 6 depicts aan embodiment of a blocking member of the conveying device of FIG. 1, in a longitudinal section.

FIGS. 5 and 6, which respectively show the conveying member 5 and the blocking member 6 individually and in the same section as FIG. 3, show the locking means and locking counter means 14 to 17.

The blocking member 6 is connected to the conveying member 5 such that it can be axially moved but is secured against rotating in relation to the threaded axis R. The conveying member 5 forms an axial guiding path for the blocking member 6. The conveying member 5 can be axially moved relative to the base along the threaded axis R and is prevented from rotating about the threaded axis R by a corresponding guiding engagement, for example a guiding engagement of the base. When the threads 8 and 9 are in engagement, the conveying member 5, and together with it the blocking member 6, is therefore axially moved in the advancing direction V when the conveying member 4 is rotary-driven, and likewise advances the piston in the reservoir in the advancing direction V during its axial movement, to deliver product. When the reservoir has been emptied, the conveying member 5 protrudes far enough out of the conveying member 4 that only the threads 8 and 9 still axially overlap with each other.

After the reservoir has been emptied, the conveying member 5 can be moved completely out of the threaded engagement quickly and with little input of energy, by the drive 3 and the conveying member 4, by rotating the conveying member 4 further by a few rotations, the number of which corresponds to the number of turns of the thread 9. The conveying member 5 and the blocking member 6 can be exchanged for a new conveying member 5 and a new blocking member 6, if they are designed as disposable parts, or, as applicable, are used again, to which end the fixation of the blocking member 6 in the blocking position has to be configured to be releasable.

If, as in some preferred embodiments, the conveying member 5 and the blocking member 6 are exchanged, then after the old piston rod has been expelled, the user grips the new combination of the conveying member 5 and blocking member 6, with the new blocking member 6 fixed to the conveying member 5 in the initial position, and axially inserts the conveying member 5 into the conveying member 4, counter to the advancing direction V. The insertion movement can be easily performed due to the elastically bending arms 11 and 12. The user merely has to press the combination of the conveying member 5 and blocking member 6 like a plunger into the conveying member 4, up to the stopper position, with a slight pressure. During this axial movement, the thread 9 elastically slides off on the thread 8, with a slight radial pressure, in accordance with its restoring bending elasticity. As soon as the conveying member 5 has reached the stopper position, the user presses the blocking member 6 counter to the advancing direction V, axially deeper into the conveying member 5, until it locks to the conveying member 5 in the blocking position. Reaching the blocking position is tactilely perceived, and, in some preferred embodiments, additionally detected by a sensor of the conveying device. The correct positioning of the blocking member 6 is also indicated to the user, e.g. optically by a display associated with the apparatus. When the blocking member 6 assumes the blocking position and the arc segments of the thread 9 can therefore no longer be bent inward out of the threaded engagement with the thread 8, a fixed and axially non-slip but still free-moving threaded engagement is ensured, such that the device is ready for delivering the product from a reservoir which has been refilled or from a new reservoir which, including its contents and piston, has been exchanged.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled

The invention claimed is:
1. A conveying device in or for an apparatus for administering a product, comprising:
 a) a base;
 b) a first conveying member which can be moved relative to the base and comprises a first thread;
 c) a second conveying member which can be moved relative to the base and comprises a second thread for a threaded engagement with the first thread;
 d) wherein the second thread extends over an axial portion of the second conveying member which is radially flexible in relation to its threaded axis, such that one of the conveying members can be axially inserted into the other in an overlap of the threads;
 e) a blocking member which can be moved relative to the base, wherein one of the blocking member and the second conveying member can be moved relative to the other into a blocking position in which the blocking member radially stiffens the second thread in the threaded engagement in the region of the flexible axial portion and thus secures the threaded engagement; and
 f) a piston rod, wherein the second conveying member and the blocking member together form the piston rod which can be moved along the threaded axis to press against a piston to advance the piston for conveying the product.

2. The conveying device according to claim 1, wherein the blocking member or the second conveying member can be moved in the axial direction into the blocking position and is axially guided.

3. The conveying device according to claim 1, wherein the second conveying member carries the blocking member.

4. The conveying device according to claim 1, wherein the blocking member is guided by the second conveying member, such that it can be axially moved but is secured against rotating in relation to the threaded axis.

5. The conveying device according to claim 1, wherein in the blocking position, the blocking member is axially fixed relative to the second conveying member in a locking engagement.

6. The conveying device according to claim 1, wherein the blocking member can be moved out of a releasable locking engagement relative to the second conveying member into the blocking position.

7. The conveying device according to claim 5, wherein a circumferential surface of the blocking member comprises one or more fixing means for creating the locking engagement, wherein the fixing means comprises recesses or bumps on the circumferential surface.

8. The conveying device according to claim 7, wherein the second conveying member comprises one or more fixing counter means for the locking engagement with the fixing means of the blocking member.

9. The conveying device according to claim 5, wherein the blocking member and the second conveying member are axially fixed to each other in the locking engagement.

10. The conveying device according to claim 1, wherein in the blocking position, the blocking member radially supports the second thread in a positive fit only, with zero force, as long as the threaded engagement is not axially loaded, and supports the second thread radially inwardly or presses the second thread into the threaded engagement radially outwardly.

11. The conveying device according to claim 1, wherein the piston rod is axially fixed to the piston, releasably fixed to the piston, or is in an axial pressing contact with the piston and acts in an advancing direction for conveying the product.

12. The conveying device according to claim 1, wherein the blocking member forms a front end for contacting the piston.

13. The conveying device according to claim 1, wherein the second conveying member and the blocking member can be telescopically and axially moved relative to each other into the blocking position.

14. The conveying device according to claim 1, wherein the blocking member protrudes out of the second conveying member and can be axially moved out of an initial position into the blocking position, deeper into the conveying member.

15. The conveying device according to claim 1, wherein the second thread in the flexible axial portion comprises at least one arc segment which extends over an angle of at most 180° about the threaded axis, and wherein if there is more than one arc segment, the segments are respectively separated from each other on the left and right in the circumferential direction.

16. The conveying device according to claim 1, the flexible axial portion comprises at least one axially extending arm and the second thread is formed on the at least one arm.

17. The conveying device according to claim 14, wherein the second conveying member comprises axially extending breaches between arc segments which are adjacent in the circumferential direction, said breaches separating the arc segments from each other.

18. The conveying device according to claim 1, wherein the second conveying member is hollow at least in the flexible axial portion.

19. The conveying device according to claim 1, wherein the second thread is an outer thread.

20. The conveying device according to claim 1, wherein the first thread is an inner thread.

21. The conveying device according to claim 1, wherein the second thread extends over a part of the axial length of the first thread.

22. The conveying device according to claim 1, wherein one of the conveying members is rotatable about the threaded axis relative to the base, and the other conveying member can be axially moved relative to the base, but is secured against rotating in relation to the threaded axis.

23. The conveying device according to claim 1, comprising a drive for automatically rotary-driving one of the conveying members.

* * * * *

UNITED STATES PATENT AND TRADEMARK OFFICE
CERTIFICATE OF CORRECTION

PATENT NO.         : 8,177,751 B2
APPLICATION NO.    : 12/685262
DATED              : May 15, 2012
INVENTOR(S)        : Roger Haenggi et al.

Page 1 of 1

It is certified that error appears in the above-identified patent and that said Letters Patent is hereby corrected as shown below:

Col. 1, Line 47, ". to be" should read --. To be--

Col. 3, Line 58, "fulfil" should read --fulfill--

Col. 4, Line 51, "regions(s)" should read --region(s)--

Col. 6, Line 3, "aan" should read --an--

Col. 6, Line 36, ". to be" should read --. To be--

Col. 9, Line 21, "– in in" should read -- - in--

Col. 10, Line 41, "entitled" should read --entitled.--

Signed and Sealed this
Eleventh Day of September, 2012

David J. Kappos
*Director of the United States Patent and Trademark Office*